(12) United States Patent
Huang (10) Patent No.: US 11,510,716 B2
(45) Date of Patent: Nov. 29, 2022

(54) NONMETALLIC IMPLANT SCREW LOCKING STRUCTURE

(71) Applicant: SHANGHAI REACH MEDICAL INSTRUMENT CO., LTD., Shanghai (CN)

(72) Inventor: Xiaomin Huang, Shanghai (CN)

(73) Assignee: Shanghai Reach Medical Instrument Co., Ltd., Shanghai (CN)

( * ) Notice: Subject to any disclaimer, the term of this patent is extended or adjusted under 35 U.S.C. 154(b) by 299 days.

(21) Appl. No.: 16/627,329

(22) PCT Filed: Jul. 12, 2018

(86) PCT No.: PCT/CN2018/095399
§ 371 (c)(1),
(2) Date: Dec. 29, 2019

(87) PCT Pub. No.: WO2019/148773
PCT Pub. Date: Aug. 8, 2019

(65) Prior Publication Data
US 2020/0138496 A1    May 7, 2020

(30) Foreign Application Priority Data
Feb. 5, 2018   (CN) .......................... 201810111346.7

(51) Int. Cl.
*A61B 17/80* (2006.01)
*A61B 17/86* (2006.01)
*A61B 17/70* (2006.01)

(52) U.S. Cl.
CPC ........ *A61B 17/866* (2013.01); *A61B 17/8052* (2013.01); *A61B 17/8605* (2013.01); *A61B 17/8625* (2013.01); *A61B 17/7059* (2013.01)

(58) Field of Classification Search
CPC .... A61B 17/8605; A61B 17/866; A61B 17/80
See application file for complete search history.

(56) References Cited

U.S. PATENT DOCUMENTS 5,868,749 A * 2/1999 Reed .................... A61B 17/866
606/76
2005/0234458 A1* 10/2005 Huebner ............ A61B 17/8061
606/71

(Continued)

FOREIGN PATENT DOCUMENTS

CN    1321094    11/2001
CN    1835718    9/2006

(Continued)

OTHER PUBLICATIONS

International Search Report in PCT/CN2018/095399, issued by ISA, dated Aug. 8, 2019.

(Continued)

*Primary Examiner* — David W Bates
(74) *Attorney, Agent, or Firm* — Zhu Lehnhoff LLP (57) ABSTRACT

The invention provides a nonmetal implant screw locking structure, which has the advantages of simple structure, novel design, simple production and processing, and convenient clinical operation. In addition, the structure of the invention can be used for orthopedic nonmetal implants such as the bone injury repair plate, spinal fusion cage, spinal fixation plate, posterior cervical single trapdoor plate, posterior cervical plate, lumbar anterior plate and lumbosacral plate, bringing good economic and social benefits gradually.

6 Claims, 9 Drawing Sheets

(56) References Cited

U.S. PATENT DOCUMENTS

2007/0162018 A1* 7/2007 Jensen ............... A61B 17/8863
　　　　　　　　　　　　　　　　　　　606/326
2013/0096631 A1* 4/2013 Leung ................ A61B 17/8605
　　　　　　　　　　　　　　　　　　　606/280
2017/0143392 A1* 5/2017 Weinzweig ...... A61B 17/00491

FOREIGN PATENT DOCUMENTS

| CN | 201624766 | 11/2010 |
|----|-----------|---------|
| CN | 103491989 | 1/2014 |
| CN | 104725771 | 6/2015 |
| CN | 206761800 | 12/2017 |
| CN | 108186102 | 6/2018 |
| GB | 2405342 | 10/2003 |

OTHER PUBLICATIONS

Written Opinion of the International Search Report in PCT/CN2018/095399, issued by ISA, dated Aug. 8, 2019.

* cited by examiner

NONMETALLIC IMPLANT SCREW LOCKING STRUCTURE

TECHNICAL FIELD

The invention relates to the technical field of medical devices for orthopedic surgery, in particular to a nonmetal implant screw locking structure.

BACKGROUND

As everyone knows, the treatment of various bone fractures, bone defects or bone tissue degeneration shall promote bone growth and fusion, and orthopedic implants such as plates, connecting rods and screw systems are required. Many previous orthopedic implants are made of metal materials. These materials have many advantages: easy disinfection, good biocompatibility, and availability of necessary fixation strength to support or fix bone tissues. However, a metal material also has the disadvantages that its compression modulus is much higher than that of cortical bones, resulting in stress shielding, reducing the formation of new bones and causing osteopenia or osteoporosis, and there is the possibility of refracture. After bone repair, these implants no longer need to be retained during patients' activity time. The implants may be taken out, and some metal implants are also allowed to be retained in the body. When they are taken out, another operation is required, which will obviously eliminate a series of secondary operation risks: alleviate the patients' pain and discomfort, and reduce the chance of infection. New injuries caused by retreatment need to be recovered, and surrounding tissues are also stimulated while the implants are taken out.

At present, new researches have introduced newer methods and improved new materials, including nonmetal implants, which have been used to treat various bone fractures and bone defects and to promote bone fusion. These nonmetal implants can be retained in the body for a long time, some implants or parts of the implants are absorbed after a certain period of time, and there are new bones growing in. Also, since the elastic modulus of products made of nonmetal materials are very close to that of bones, the stress shielding for the growth of new bones is eliminated, the bone fusion and healing are accelerated, long-term retention in vivo without stress shielding leads to osteoporosis, so the nonmetal materials are more suitable for the fusion treatment of bone fractures, bone defects and degeneration. These new nonmetal materials have more significant advantages than metal materials. Of course, there are also aspects that need to be further improved. For example, the lower mechanical strength of nonmetal materials, the weak grasping force of nonmetal screws on bones and the lack of locking force of screws and plate products cannot meet the requirements for complete installation of product structure and stable fixation of bones.

Because of the above problems, the current applications of nonmetal materials in orthopedics are very limited. The invention improves the mechanical strength of materials by combination of different nonmetal materials on the basis of previous researches to meet the requirement for complete installation of nonmetal devices and improve their fixation strength of bones through different combinations of metal screws and nonmetal products with special design and surgical methods. Thus, the application prospect of nonmetal materials in orthopaedics is widened.

At present, the nonmetal implants available on the market are mainly locked by expansion, circlips or some metal materials. But such products are complex in processing, which increases the cost and adds to the patients' financial burden; moreover, the operation is cumbersome, the operation time is prolonged, and the risk of various surgical complications is increased.

SUMMARY OF THE INVENTION

The invention is related to an orthopedic implant and a treatment method of bone defects. Specifically, the invention is an orthopedic implant produced by applying a new nonmetal material, and its design is improved to promote bone growth in treated positions. The nonmetal implant screw locking structure is designed to overcome the disadvantages of looseness and receding of the screws depending on the elastic attribute of the nonmetal implant itself by automatically using the self-tapping function of the metal screws on the nonmetal implant during installation and to achieve the locking between the screws and the nonmetal implant, with simple installation for surgical operation and reliable structure.

To achieve the above purpose, the invention provides a nonmetal implant screw locking structure, which is implemented by the following scheme: comprising a nonmetal implant and metal screws; wherein fixing holes are arranged in the nonmetal implant; bone threads are arranged in the front of the metal screw, and sharp threads or sharp-pointed objects are arranged at the tail of the metal screw.

Further, the fixing holes are straight holes or conical holes or threaded holes.

Further, the sharp threads or sharp-pointed objects at the tail of the metal screws result in tapping and cutting on the nonmetal implant in the process of screwing the nonmetal implant into a bone structure by the metal screws along the fixing hole during installation, and the sharp threads or sharp-pointed objects are completely clamped in the nonmetal implant to fix the nonmetal implant to the bone structure.

Further, the outside diameter of the threads of the metal screws is greater than the diameter of the fixing holes, and the inside diameter of the threads at the tail of the metal screws is reduced.

Further, the threads of the metal screws cut the fixing holes by tapping and form threaded hole channels in the process of screwing the nonmetal implant into the bone structure by the metal screws along the fixing holes during installation, and the metal screws are completely clamped in the nonmetal implant to fix the nonmetal implant to the bone structure during locking.

Further, the metal screws are full bone threads; the nonmetal implant materials comprise non-absorbable biomaterials such as PEEK, PEEK+carbon fiber, PEEK+calcium silicate, PEEK+HA, PEKK, PEKK+carbon fiber, PEKK+calcium silicate and macromolecular polyethylene, as well as absorbable biomaterials such as levolactic acid, D,L-Lactide, glycollic acid and trimethylene carbonate Further, the nonmetal implant consists of raw materials with the following parts by weight: 40-70 parts of PEEK, and 30-40 parts of calcium silicate and/or macromolecular polyethylene. The preferred composition is 50-70 parts of PEEK and 30-40 parts of calcium silicate and macromolecular polyethylene, wherein the wt % of calcium silicate and macromolecular polyethylene is 3:1.

Further, the nonmetal implant also comprises 10-15 parts of artificial bone powder. Preferably, the nonmetal implant comprises 11-12 parts of artificial bone powder; the artificial bone powder is nanoscale bone powder.

Further, the nonmetal implant also comprises 0.1-0.5 part of microcapsules.

Further, the microcapsule is in a core-shell structure, the core layer is sodium carbonate, the shell layer is chitosan, and the surface of the shell layer is also covered with calcium chloride. The microcapsule has a slow release effect. If the screws crack, it will result in microcapsule rupture, thus generating calcium carbonate, filling the cracks and restoring the strength of the nonmetal implant. At the beginning of use, the microcapsule on the surface of the nonmetal implant is ruptured, generating calcium carbonate and filling the gap between the screw and the plate, and then improving the effect of binding between the screws and the plate.

Compared with the prior art, the invention has the advantages that:

(1) It is simple in structure, novel in design, simple in production and processing, and very convenient in clinical operations. In addition, the structure of the invention can be used for orthopedic nonmetal implants such as the bone injury repair plate, spinal fusion cage, spinal fixation plate, posterior cervical single trapdoor plate, posterior cervical plate, lumbar anterior plate and lumbosacral plate, bringing good economic and social benefits gradually.

(2) Using the nonmetal implant with light weight and elastic modulus similar to that of cortical bones of a human body, the stress shielding is significantly reduced after implantation, stress concentration is avoided, and degeneration of contiguous vertebral bodies is delayed. Compared with the current titanium alloy products, it is transparent, elastic and better in operation adaptability.

(3) After operation, the progress of bone healing can be clearly observed by X-ray.

(4) Addition of a proper amount of artificial bone powder into the nonmetal implant can not only improve the strength of the nonmetal implant, but also improve the surgery adaptability and meet the requirements for clinical quickness and safety.

(5) A proper quantity of microcapsules is added to the nonmetal implant to allow the nonmetal implant to have the self-repairing function, and the effect of binding between the screws and the plate is also improved. And the added amount is low, the cost is also low, and an unexpected effect is achieved.

BRIEF DESCRIPTION OF THE DRAWINGS

In order to explain the embodiments of the invention or the technical scheme in the prior art more clearly, a brief introduction to the drawings to be used in the description of the embodiments or the prior art will be given below. Apparently, the drawings in the following description are only some embodiments of the utility model. For those of ordinary skill in the art, other drawings can also be obtained according to these drawings without any creative work.

DETAILED DESCRIPTION OF THE PREFERRED EMBODIMENTS

In order to achieve the purpose of the invention, the invention will be further described below in combination with Embodiment 1.

Figure 1:
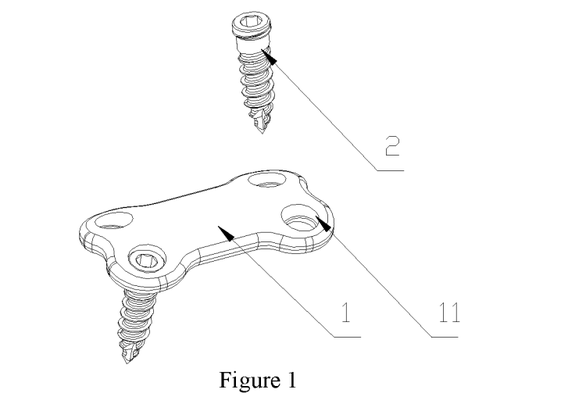
FIG. 1 is a structure diagram of the invention.
Figure 2A:
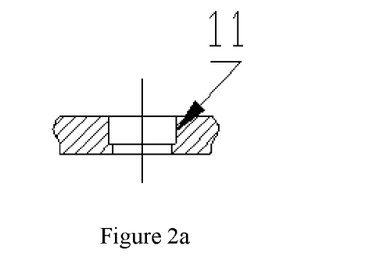
FIG. 2a to FIG. 2f are schematic diagrams of the hole shape of the nonmetal implant of Embodiment 1 of the invention.
Figure 2B:
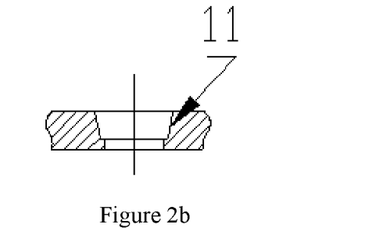
Figure 2C:
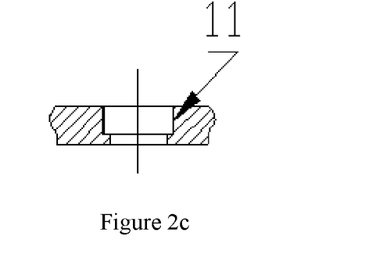
Figure 2D:
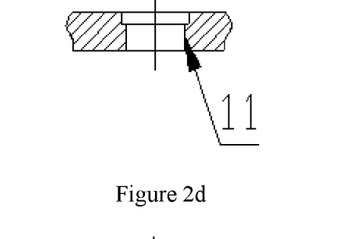
Figure 2E:
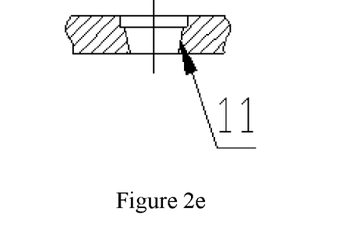
Figure 2F:
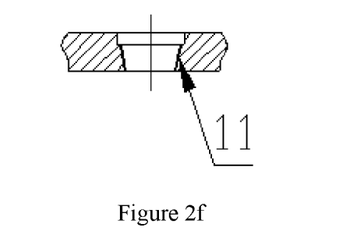

As shown in FIG. 1, a nonmetal implant screw locking structure is proposed in this embodiment, comprising a nonmetal implant 1 and metal screws 2; wherein a plurality of fixing holes 11 are arranged in the nonmetal implant 1; bone threads are arranged in the front of the metal screws 2, and sharp threads or sharp-pointed objects are arranged at the tail of the metal screws.

As shown in FIG. 2a to FIG. 2f, the hole shape of the fixing holes 11 in the nonmetal implant 1 is straight or conical or short threaded.

Figure 3A:
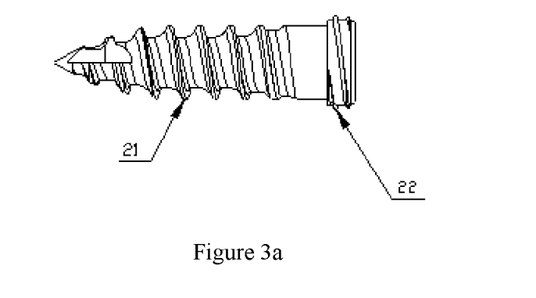
FIG. 3a and FIG. 3b are structure diagrams of the screw structure of Embodiment 1 of the invention.
Figure 3B:
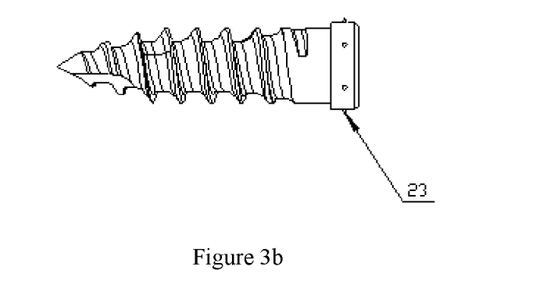
Figure 4A:
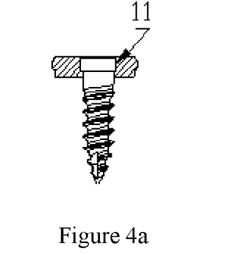
FIG. 4a to FIG. 4f are schematic diagrams of the fit of the screws of Embodiment 1 of the invention with the sharp threads or sharp-pointed objects removed.
Figure 4B:
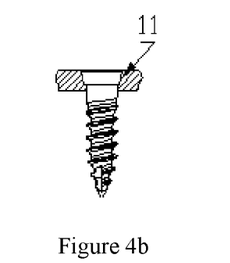
Figure 4C:
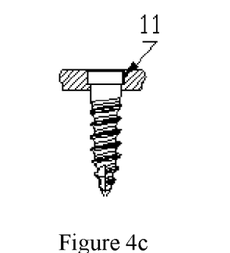
Figure 4D:
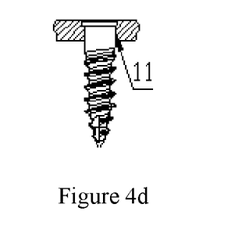
Figure 4E:
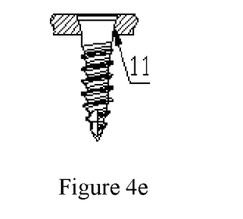
Figure 4F:
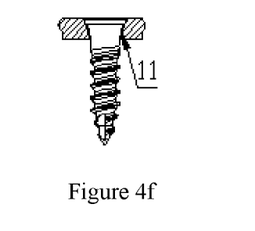

As shown in FIG. 3a and FIG. 3b, bone threads 21 are arranged in the front of the metal screw 2, sharp threads 22 or sharp-pointed objects 23 are arranged at the tail of the metal screw 2, the pitch of the sharp threads 22 shall be the same as that of the bone threads 21, and the sharp threads 22 may be multi-start screw thread lines.

Figure 5A:
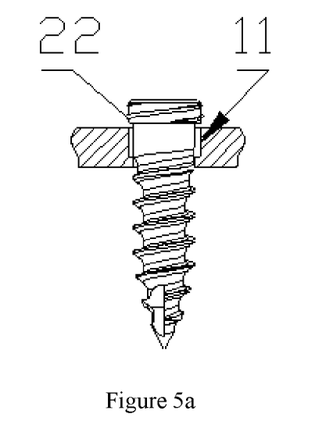
FIG. 5a to FIG. 5b are schematic diagrams of the locking of Embodiment 1 of the invention.
Figure 5B:
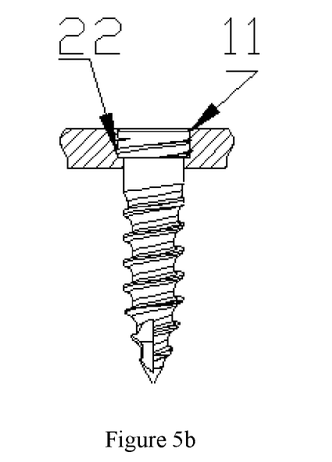

As shown in FIG. 4a to FIG. 4f, the shape of the tail of the metal screw 2 with the sharp threads 22 or the sharp-pointed objects 23 removed shall be matched with or slightly larger than the shape of the fixing holes 11 in the nonmetal implant 1; combined with those shown in FIG. 5a to FIG. 5b, the shape of the sharp threads 22 or the sharp-pointed objects 23 at the tail of the metal screw 2 shall be slightly larger than the shape of the fixing holes 11 to ensure that the sharp threads 22 or the sharp-pointed objects 23 at the tail tap the nonmetal implant 1 and are engaged with the nonmetal implant 1 after the metal screws 2 are screwed into the bone. Due to the extrusion of metal to non-metal, the generated chips will hold the sharp threads 22 or the sharp-pointed objects 23 on the metal screws 2 tightly so that the metal screws 2 are firmly locked to the nonmetal implant 1, thus achieving the functions of locking, looseness prevention and receding prevention.

The nonmetal implant consists of raw materials with the following parts by weight: 40-70 parts of PEEK, and 30-40 parts of calcium silicate and/or macromolecular polyethylene. Specifically, the nonmetal implant 2 can be prepared from 60 parts of PEEK, 30 parts of calcium silicate and 10 parts of macromolecular polyethylene.

Using the above materials, the nonmetal implant 1 can avoid stress concentration well. In addition, the structure proposed in this embodiment can avoid the weak grasping force of the nonmetal screws on the bones and the lack of locking force of screws and plate products, which cannot meet the requirement of complete installation of the product structure to achieve the purpose of stable fixation of the bones.

The invention will be further described below in combination with Embodiment 2.

Figure 6:
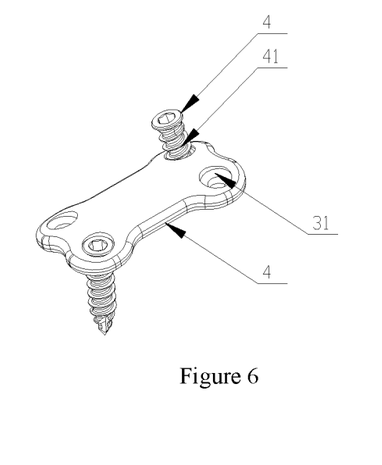
FIG. 6 is a structure diagram of Embodiment 2 of the invention.

As shown in FIG. 6, the nonmetal implant screw locking structure consists of a nonmetal implant 3 and metal screws 4. A plurality of fixing holes 31 are arranged in the nonmetal implant 3. The metal screws 4 are full bone threads 41, and the materials of the nonmetal implant 3 include, but not limited to, PEEK (polyetheretherketone), PEEK+carbon fiber, PEEK+calcium silicate, PEEK+HA (hydroxyapatite), PEKK (polyetherketoneketone), macromolecular polyethylene, PEKK+carbon fiber, PEKK+calcium silicate, as well as absorbable materials for a human body, such as levolactic acid, D,L-Lactide, glycollic acid and trimethylene carbonate.

Figure 7A:
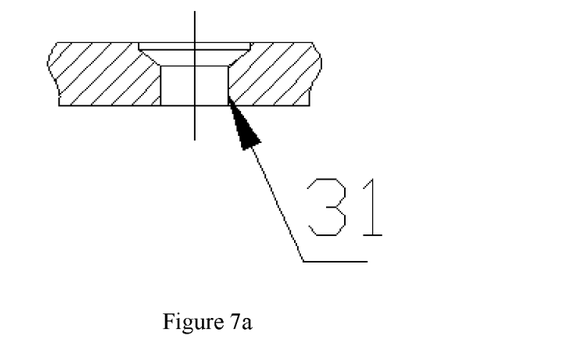
FIG. 7a and FIG. 7b are schematic diagrams of the hole shape of the nonmetal implant of Embodiment 2 of the invention.
Figure 7B:
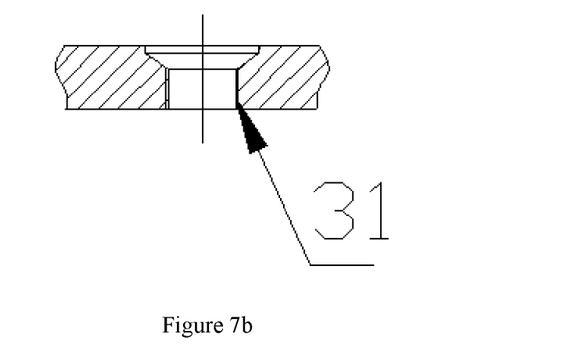

As shown in FIGS. 7a and 7b, the shape of the fixing holes 31 in the nonmetal implant 3 is straight or short threaded.

Figure 8A:
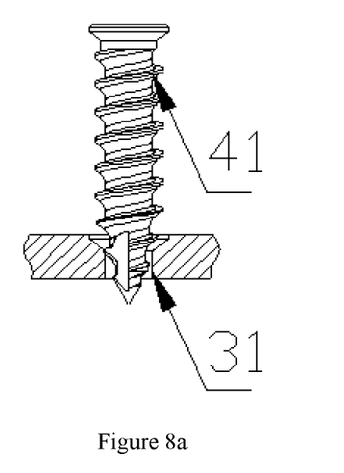
FIG. 8a and FIG. 8b are schematic diagrams of the locking of Embodiment 2 of the invention.
Figure 8B:
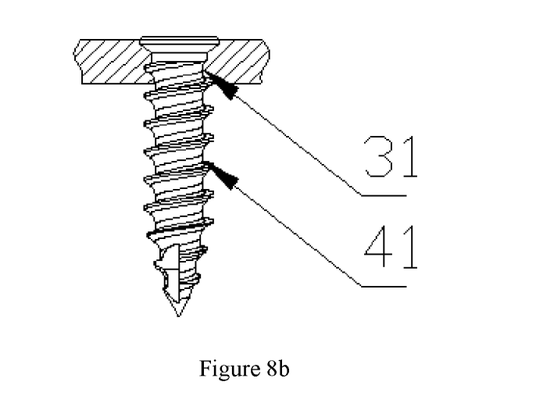

As shown in FIGS. 8a and 8b, the inside diameter of the threads of the metal screw 4 shall be matched with or slightly smaller than the diameter of the fixing holes 31 in the implant 3. The outside diameter of the threads of the metal screws 4 is larger than the diameter of the fixing holes 31 in the implant 3, and in this way, it ensures that the full bone threads 41 tap the nonmetal implant 3 and are engaged with the nonmetal implant 3 in the process of screwing the metal screws 4 into the bones. Since the threads 41 at the tail of the metal screw is in a closed state with the inside diameter increased and the thread form thickened, the forepart of the tapped nonmetal implant 3 is extruded so that the metal screws 4 is firmly locked to the nonmetal implant 3, thus achieving the functions of locking, looseness prevention and receding prevention.

In this embodiment, the mechanical strength of the material is improved by combination of different nonmetal materials: such as different proportion structures of PEEK+CF (carbon fiber) and the like to meet the requirement of complete installation of nonmetal devices and to improve the fixation strength of bones through different combinations of metal screws and nonmetal products with special design and surgical approaches.

Moreover, the nonmetal implant screw locking structure is designed to overcome the disadvantages of looseness and receding of the screws depending on the elastic attribute of the nonmetal implant itself by automatically using the self-tapping function of the metal screws on the nonmetal implant during installation and to achieve the locking between the screws and the nonmetal implant, with simple installation for surgical operation and reliable structure.

It can be seen that the product made of the PEEK carbon fiber implant grade material meets the industrial standards and biomechanical requirements of cervical plates. The product has light weight and elastic modulus similar to cortical bones of a human body. After implantation, the product can significantly reduce stress shielding, avoid stress concentration and delay the degeneration of contiguous vertebral bodies. Compared with the current titanium alloy products, the product is transparent, elastic and better in operation adaptability.

The invention will be further described below in combination with Embodiment 3.

In this embodiment, the nonmetal implant screw locking structure is the same as that in Embodiment 2, which will not be elaborated herein. For details, please refer to Embodiment 2.

Unlike Embodiment 2, in this embodiment, the nonmetal implant consists of raw materials with the following parts by weight: 40-70 parts of PEEK, and 30-40 parts of calcium silicate and/or macromolecular polyethylene. The nonmetal implant also comprises 10-15 parts of artificial bone powder. The nonmetal implant also comprises 0.1-0.5 part of microcapsules. The microcapsule is in a core-shell structure, the core layer is sodium carbonate, the shell layer is chitosan, and the surface of the shell layer is also covered with calcium chloride.

Specifically, the nonmetal implant adopts the nonmetal implant 2 prepared from 50 parts of PEEK, 30 parts of calcium silicate, 12 parts of artificial bone powder and 0.3 parts of microcapsules.

Addition of an appropriate amount of artificial bone powder into the nonmetal implant can not only improve the strength of the nonmetal implant, but also improve the surgery adaptability and meet the requirements for clinical quickness and safety. The microcapsule has a slow release effect. If the screws crack, it will result in microcapsule rupture, thus generating calcium carbonate, filling the cracks and restoring the strength of the nonmetal implant. At the beginning of use, the microcapsule on the surface of the nonmetal implant is ruptured, generating calcium carbonate and filling the gap between the screw and the plate, and then improving the effect of binding between the screws and the plate.

To sum up, the nonmetal implant screw locking structure proposed by the invention consists of the implant and the screws, wherein the implant is nonmetal, and the screws are metal screws. There are fixing holes in the implant, and the shape of the fixing holes is straight or threaded. The metal screws are basically full thread screws, and the threads are closed in a part close to the screw tail. The threads of the metal screws will cut the fixing holes by tapping and form threaded hole channels in the process of screwing the metal screws into the bone structure along the fixing holes of the implant during installation because the outside diameter of the threads of the metal screws is greater than the diameter of the fixing holes. Since the inside diameter of the threads 41 at the tail of the metal screw is reduced with the screw threads thickened, the metal screws are completely engaged with the implant when finally locked to achieve the function of locking, and the implant is firmly fixed to the bone structure.

In addition, the steel plate made of a new material is in a pre-bent morphological structure with an extra-large bone grafting window, innovative and reliable locking mechanism, self-tapping/self-drilling screws and fixed/adjustable angle so that mixed and fixed configurations such as restrictions and semi-restrictions in surgery can be satisfied. In terms of fixation function, the steel plate has the excellent characteristics of high-quality anterior cervical plates currently available on the market. Moreover, disposable sterilized packages are used to reduce the surgical infection rate increase due to the previously repeated disinfection and use of titanium alloy implants, which also facilitates the requirement for emergency operation of cervical spine trauma, and saves the disinfection time of operation and the manpower and financial costs of dealers and hospitals for disinfection and sterilization. It achieves the purposes of timeliness, accuracy and emergency treatment and meets the clinical requirements for quickness, safety and effective fixation. Disposable matching tools are provided and developed to change the operation distribution mode and cater to domestic and foreign market demands.

Figure 9:
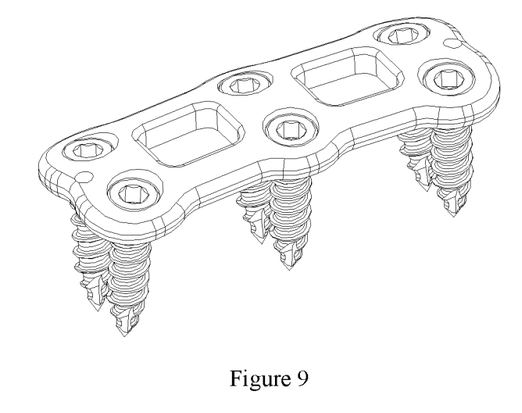
FIG. 9 is an application diagram of the invention on a spine plate.
Figure 10:
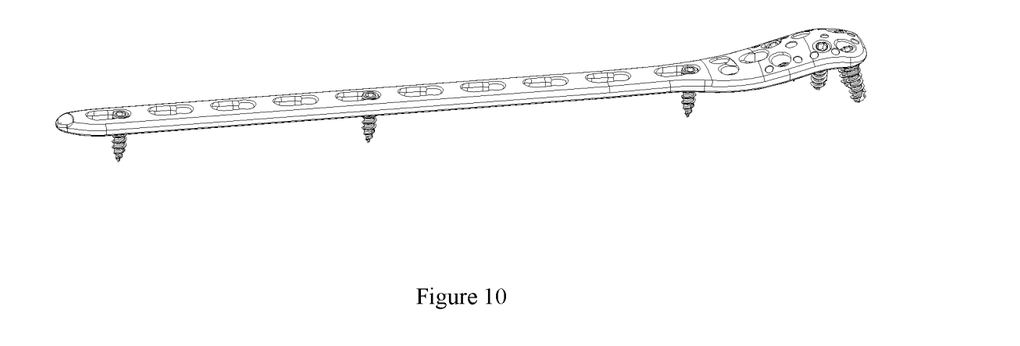
FIG. 10 is an application diagram of the invention on a bone injury repair plate.
Figure 11:
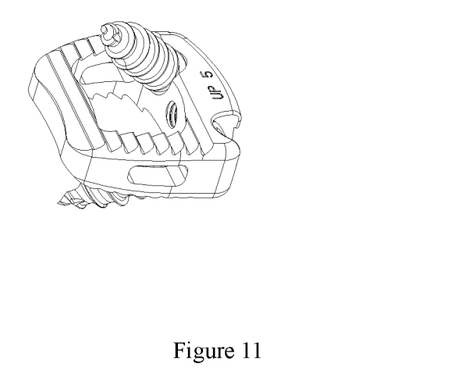
FIG. 11 is an application diagram of the invention on a fusion device.
Figure 12:
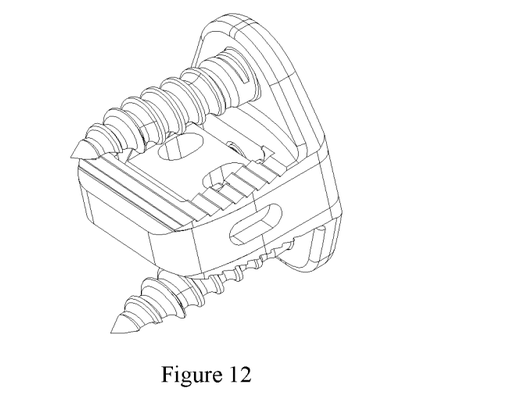
FIG. 12 is an application diagram of the invention on a fusion device with a plate.
Figure 13:
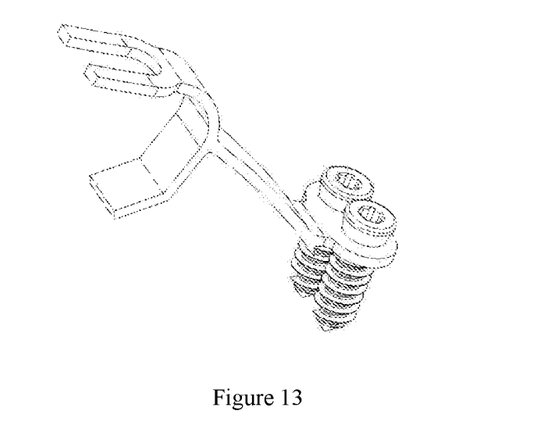
FIG. 13 is an application diagram of the invention on a posterior cervical single trapdoor plate.
Figure 14:
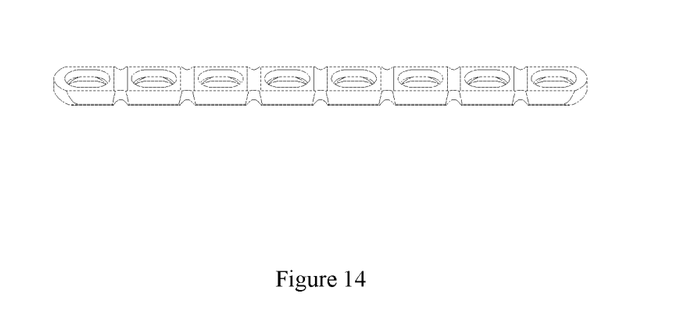
FIG. 14 is an application diagram of the invention on a posterior cervical plate.
Figure 15:
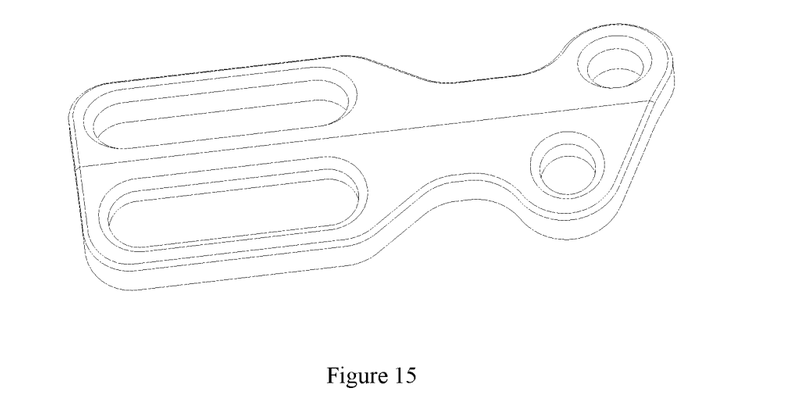
FIG. 15 is an application diagram of the invention on a lumbar anterior plate.
Figure 16:
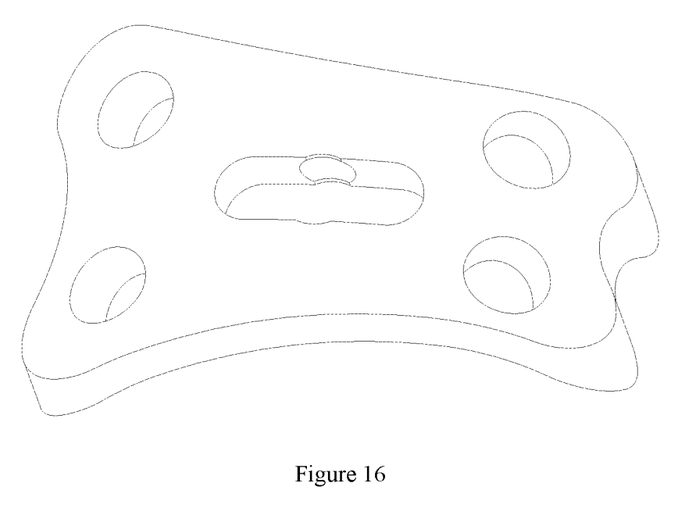
FIG. 16 is an application diagram of the invention on a lumbosacral plate.

The nonmetal implant screw locking structure put forward by the invention can also be used for the spine plate (as shown in FIG. 9), the bone injury repair plate (as shown in FIG. 10), the fusion device (as shown in FIG. 11), the fusion device with plate (as shown in FIG. 12), the posterior cervical single trapdoor plate (as shown in FIG. 13), the posterior cervical plate (as shown in FIG. 14), the lumbar anterior plate (as shown in FIG. 15) and the lumbosacral plate (as shown in FIG. 16).

Although the above drawings and descriptions have described the invention in detail, these drawings and descriptions should be considered to be illustrative rather than limiting in characteristics. It should be understood that this only indicates and illustrates better embodiments, and therefore, protection of all changes and modifications falling within the protection scope of the invention is required.

The above description of the disclosed embodiments enables those skilled in the art to realize or use the utility model. Various modifications to these embodiments will be obvious to those skilled in the art, and the general principle defined herein can be realized in other embodiments without departing from the spirit or scope of the utility model. Therefore, the utility model will not be limited to these embodiments shown herein, but will conform to the widest range consistent with the principles and novel features disclosed herein.

The invention claimed is:

1. A nonmetal implant screw locking structure comprising:
   a nonmetal implant having a plurality of fixing holes formed therein and being formed from raw materials containing, per 100 parts by weight of the raw materials, 40-70 parts by weight of PEEK, 30-40 parts by weight of at least one material selected from calcium silicate and macromolecular polyethylene, and 0.1-0.5 parts by weight of microcapsules, each of the microcapsules having a core-shell structure including a core layer of sodium carbonate, a shell layer of chitosan, and calcium chloride covering a surface of the shell layer; and
   a plurality of metal screws each of which can be inserted into one of the fixing holes, each of the screws having a bone screw thread formed on a front part of the screw for threaded engagement with a bone to secure the implant to the bone.

2. The implant screw locking structure according to claim 1 wherein the raw materials contain 10-15 parts by weight of artificial bone powder per 100 parts by weight of the raw materials.

3. The implant screw locking structure according to claim 1 wherein each of the screws has a hole tapping portion formed on a tail of the screw for tapping one of the fixing holes, each hole tapping portion comprising sharp multi-start screw threads formed on the tail of the screw for engaging with an upper end of one of the fixing holes of the implant to secure the screw in the implant.

4. A nonmetal implant screw locking structure comprising:
   a nonmetal implant which has a plurality of fixing holes formed therein and which is formed from raw materials containing, per 100 parts by weight of the raw materials, 40-70 parts by weight of PEEK, 30-40 parts by weight of at least one material selected from calcium silicate and macromolecular polyethylene, and 0.1-0.5 parts by weight of microcapsules which form calcium carbonate when ruptured; and
   a plurality of metal screws each of which can be inserted into one of the fixing holes in the implant for securing the implant to a bone, each of the screws having a bone screw thread formed on a front part of the screw for threaded engagement with a bone to secure the implant to the bone.

5. The implant screw locking structure according to claim 4 wherein each of the screws has a hole tapping portion formed on a tail of the screw for tapping one of the fixing holes, each hole tapping portion comprising sharp multi-start screw threads formed on the tail of the screw for engaging with an upper end of one of the fixing holes of the implant to secure the screw in the implant.

6. The implant screw locking structure according to claim 4 wherein the raw materials contain 10-15 parts by weight of artificial bone powder per 100 parts by weight of the raw materials.

* * * * *